United States Patent [19]
Kim

[11] Patent Number: 5,676,663
[45] Date of Patent: Oct. 14, 1997

[54] CONE BIOPSY INSTRUMENT

[76] Inventor: David S. Kim, 5343 Manitowac Dr., Rancho Palos Verdes, Calif. 90275

[21] Appl. No.: 560,276

[22] Filed: Nov. 21, 1995

[51] Int. Cl.$^6$ .................................................. A61B 17/39
[52] U.S. Cl. ........................................ 606/45; 606/49
[58] Field of Search ............................. 606/27, 28, 29, 606/30, 31, 32, 33, 34, 35, 36, 37, 38, 39, 40, 41, 42, 43, 44, 45, 46, 47, 48, 49, 50, 51, 52

[56] References Cited

U.S. PATENT DOCUMENTS

| | | |
|---|---|---|
| 3,357,422 | 12/1967 | Creelman . |
| 3,628,522 | 12/1971 | Kato . |
| 3,943,916 | 3/1976 | Vadas . |
| 4,168,698 | 9/1979 | Ostergard . |
| 4,887,593 | 12/1989 | Wiley et al. ................ 606/45 |
| 4,924,882 | 5/1990 | Donovan ................ 606/45 X |
| 5,047,042 | 9/1991 | Jerath . |
| 5,207,686 | 5/1993 | Dolgin ................ 606/47 X |
| 5,324,288 | 6/1994 | Billings et al. . |
| 5,338,317 | 8/1994 | Hasson et al. . |
| 5,339,799 | 8/1994 | Kami et al. . |
| 5,344,428 | 9/1994 | Griffiths . |
| 5,349,954 | 9/1994 | Tiemann et al. . |
| 5,352,737 | 10/1994 | Rodak et al. . |
| 5,354,311 | 10/1994 | Kambin et al. . |
| 5,370,659 | 12/1994 | Sakashita . |
| 5,372,124 | 12/1994 | Takayama et al. . |
| 5,383,471 | 1/1995 | Funnell . |
| 5,383,888 | 1/1995 | Zvenyatsky et al. . |
| 5,385,570 | 1/1995 | Chin et al. . |
| 5,392,789 | 2/1995 | Slater et al. . |
| 5,394,885 | 3/1995 | Francese . |
| 5,395,313 | 3/1995 | Naves et al. . |
| 5,395,364 | 3/1995 | Anderhub et al. . |
| 5,395,369 | 3/1995 | McBrayer et al. . |
| 5,395,386 | 3/1995 | Slater . |
| 5,396,900 | 3/1995 | Slater et al. . |
| 5,397,320 | 3/1995 | Essig et al. ................ 606/45 |
| 5,403,310 | 4/1995 | Fischer ................ 606/45 |
| 5,403,342 | 4/1995 | Tovey et al. . |
| 5,411,519 | 5/1995 | Tovey et al. . |
| 5,415,182 | 5/1995 | Chin et al. . |
| 5,419,220 | 5/1995 | Cox . |
| 5,419,339 | 5/1995 | Palmer . |
| 5,421,346 | 6/1995 | Sanyal . |
| 5,421,347 | 6/1995 | Enstrom . |
| 5,423,844 | 6/1995 | Miller . |
| 5,423,854 | 6/1995 | Martin et al. . |
| 5,425,731 | 6/1995 | Daniel et al. . |
| 5,433,725 | 7/1995 | Christian et al. . |
| 5,439,478 | 8/1995 | Palmer . |
| 5,443,475 | 8/1995 | Auerbach et al. . |
| 5,486,173 | 1/1996 | Vancaillie ................ 606/45 |
| 5,554,159 | 9/1996 | Fischer ................ 606/45 |

OTHER PUBLICATIONS

Pearce, Electrosurgery, Wiley 1986, pp. 18–23.
Olsen Electrosurgery, Inc. catalog, pp. 8 & 13.
D M Luesley et al., Loop diathermy excision of the cervical transformation zone in patients with abnormal cervical smears, British Medical Journal 1990.
Walter Prendiville et al., Large loop excision of the transformation zone.
(LLETZ). A new method of management for women with cervical intraepithelial neoplasia, British Journal of Obstetrics and Gynaecology, Sep. 1989, vol. 96, pp. 1054–1060.

(List continued on next page.)

*Primary Examiner*—Jennifer Bahr
*Assistant Examiner*—Sonya Harris-Ogugua
*Attorney, Agent, or Firm*—Pretty, Schroeder & Poplawski

[57] ABSTRACT

A cone biopsy instrument having a cuff of electrical insulating material, a core positioned within the cuff and having an electrical conductor, a wire carrier of electrical insulating material and having a plurality of radially projecting arms, an electrically conducting wire connected between a wire carrier arm and the core, an implant sleeve freely rotating on the swaged portion of the core between the wire carrier and tip, and a cervical guide tip of electrical insulating material carried on the core.

8 Claims, 2 Drawing Sheets

OTHER PUBLICATIONS

Paul F. Whiteley, et al., Treatment of cervical intraepithelial neoplasia: Experience with the low-voltage diathermy loop, American Journal Obstetrics and Gynecology, May 1990, vol. 162, pp. 1272–1277.

Author unknown, Electrosurgery and Lasers, Special Instrumentation, date unknown, pp. 116–120.

Author unknown, Loop Electrosurgical Excision Procedure, Preinvasive Diseases of the Female Lower Genital Tract, date unknown, pp. 240–243.

1

CONE BIOPSY INSTRUMENT

BACKGROUND OF THE INVENTION

This invention relates to a biopsy instrument for the loop electrosurgical excision procedure (LEEP). In this procedure a portion of the cervix is resected for diagnosis and treatment of histologic abnormalities. The abnormalities usually diagnosed are of an infectious etiology and dysplasia of the cervical epithelium, which may lead to cancer.

Historically, a knife cone biopsy, the gold standard of cone biopsy, was performed if there were a suspicion of cervical cancer noted on the colposcopy and biopsy. The knife cone biopsy should produce an intact cone shaped tissue for pathologic evaluation. The major disadvantages of knife cone biopsy are that the procedure may be associated with a large volume of blood loss and that the procedure must be done in a hospital under general anesthesia. With the recent development of the electrosurgical technology, a wire loop with current running at a specific frequency and current density can be used to cut tissues without a significant blood loss. This technology is applied in the LEEP which is usually performed at a clinic.

Multiple disadvantages in the use of the loop are encountered during LEEP. Initially, the tissues obtained during the standard LEEP cone biopsy are fragmented and disorganized. Therefore, the pathologic diagnosis may be difficult. Secondly, the endocervical canal may not be accurately removed because each patient has a uniquely positioned cervix. An adequate cervical cone biopsy with a loop may take as much as 5–10 minutes, during which time bleeding may be excessive or a false passage may be created. Lastly, and most importantly, the repeated lateral movement of the loop to resect a portion of a large cervix may be dangerous, resulting in injury to the lateral vaginal wall.

Therefore, the objective of the present invention is to provide a cone biopsy instrument which will reduce or eliminate the above problems, yet combine the advantages of the knife cone biopsy procedure and LEEP. The instrument of the present invention produces an intact tissue sample, and is simplistic in use. Most importantly, it is safe to use. Other objects, advantages, features and results will be discussed in the course of the following description.

SUMMARY OF THE INVENTION

The presently preferred embodiment of the invention includes a cuff of electrical insulating material, a core positioned within the cuff and having an electrical conductor, a wire carrier of electrical insulating material and having at least one radially projecting arm, and an electrically conducting wire connected between the wire carrier arm and the wire core at an oblique angle to the core. Preferably, the cuff and core are fixed relative to one another, and are rotatable in a handle which provides electrical power to the wire.

The biopsy instrument preferably also includes a cervical guide tip of electrical insulating material carried on the core adjacent to the wire, an implant sleeve freely rotating on the core between the wire carrier and cervical guide tip, and a second radially projecting arm on the wire carrier with a tissue cutting blade at the outer end of the second arm. Preferably, the wire carrier is affixed to the cuff.

DESCRIPTION OF THE PREFERRED EMBODIMENT

Figure 1:
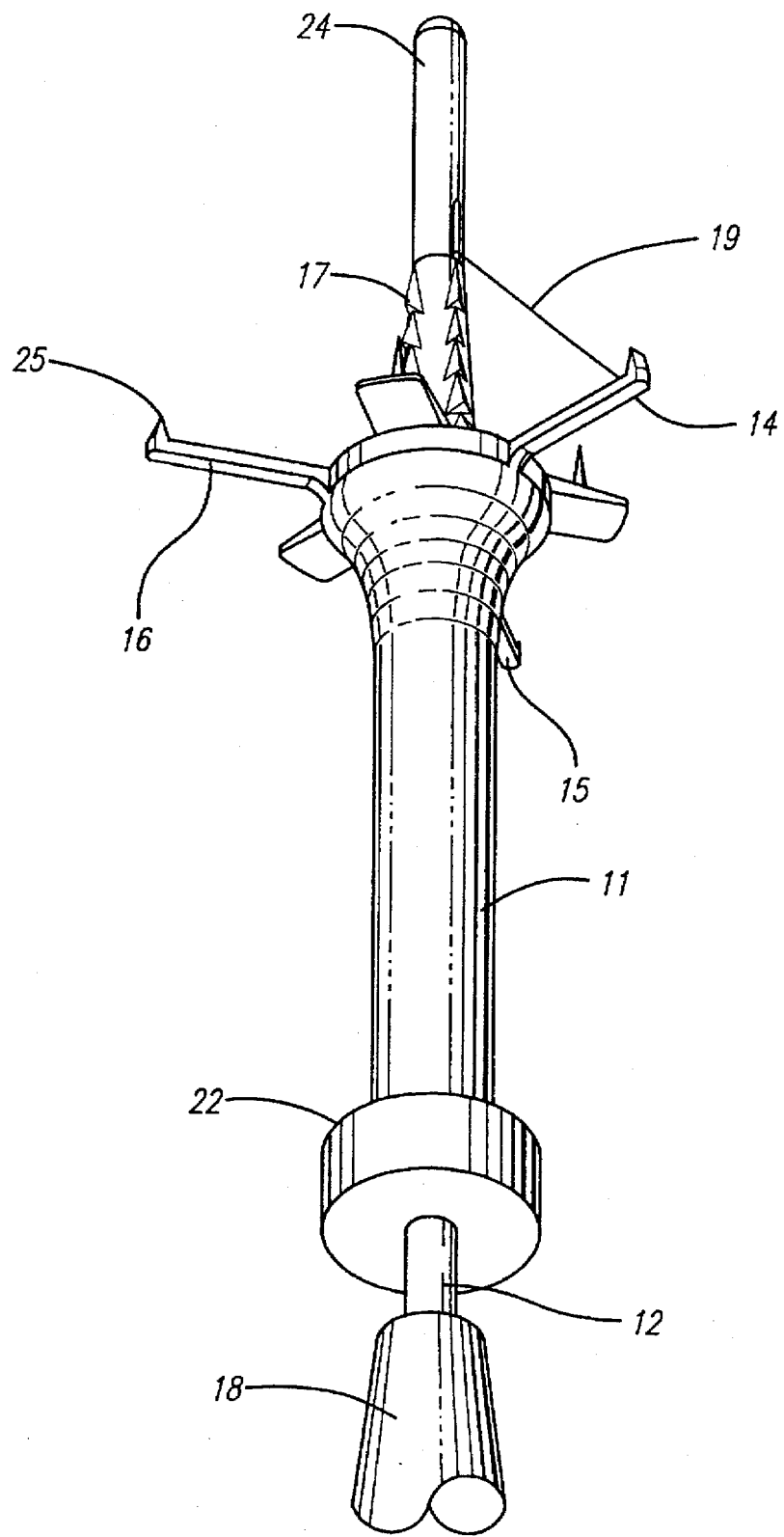
FIG. 1 is a perspective view of a cone biopsy instrument incorporating the presently preferred embodiment of the invention.
Figure 2:
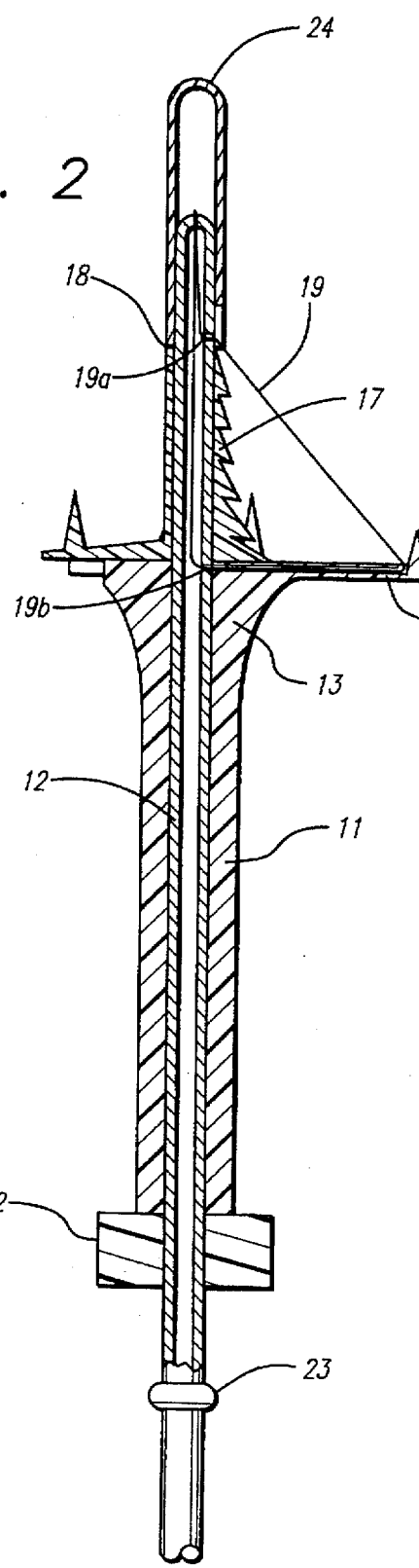
FIG. 2 is a longitudinal sectional view of the instrument of FIG. 1.
Figure 3:
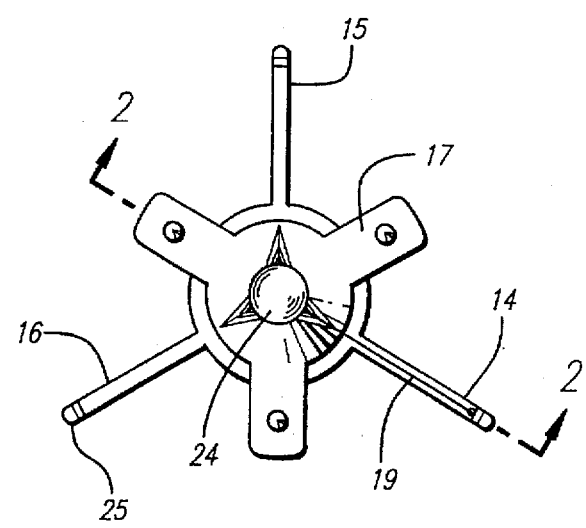
FIG. 3 is an inner end view of the instrument of FIG. 1.
Figure 4:
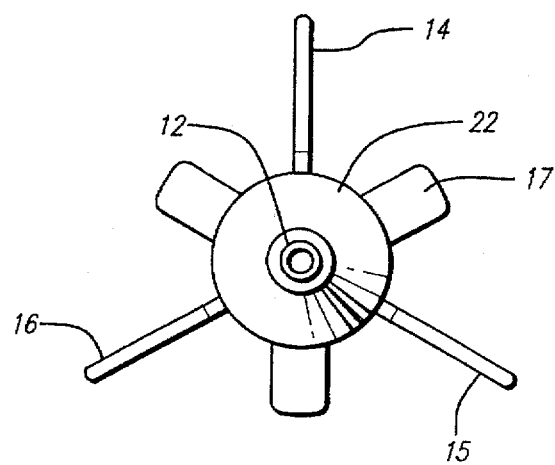
FIG. 4 is an outer end view of the instrument of FIG. 1.

The preferred embodiment of the instrument includes a cuff 11 with a core 12 therein; with the core and cuff fixed relative to one another for rotation as a unit. A wire carrier 13 is positioned at the inner end of the cuff 11, and in the embodiment illustrated is formed as a part of the cuff. The wire carrier has at least one radially projecting arm 14, and preferably two additional arms 15, 16, equally spaced around the core.

An implant sleeve 17 is positioned on the core 12 and is freely rotatable with respect to the core and the cuff. A wire 19 is connected between the core 12 and the outer end of the arm 14 at an oblique angle to the core so that the wire defines a conical surface when the instrument is rotated about the axis of the core. The core preferably is a metal tube with lateral opening 19a and 19b, with the wire 19 running down from the tip of the core 12, out through the opening 19b and through a passage in the arm 14 to near the outer end of the arm 14. The wire then moves through a passage in the arm, through the opening 19a, and finally up through the core to the tip. The core tip and the two ends of the wire are crimped or otherwise joined together to provide an electrical connection to the wire from the core.

The core 12 desirably has a knob 22 formed at the end opposite the tip for ease of rotating the core and cuff. An annular bead 23 or other suitable construction is provided adjacent to the lower end of the core for an electrical connection to a handle 18 of an electric power source. The upper end 24 of the instrument preferably is formed of an electrical insulating material which slides over the core, and extending a sufficient distance to be inserted into the cervix and guide the positioning of the instrument.

Desirably, the implant sleeve has barbs which assist in maintaining the position of the tissue during the biopsy procedure. Also, a cutting blade 25 may be carried at the end of one or more of the arms of the wire carrier.

In operation, the handle of a conventional electrosurgical power supply is connected at the lower end of the core 12, with electrical connection through the core to the wire 19.

After the patient is given paracervical anesthesia, the cervical guide tip 24 is placed into the cervix with the cutting wire 19 at 12 o'clock. By gentle pushing of the instrument against the cervix, barbs of the sleeve 17 will implant into the cervix to hold the tissue. The electrical power cable with handle and switches for selecting coagulating current and cutting current is pushed onto the lower end of the core of the instrument. While the current is on, the cervical guide is pushed further into the cervical canal until the spikes of the sleeve 17 are implanted in the cervix for stabilization of the specimen to be resected. The handle of the power source is then held firmly with the non-dominant hand. The knob 22 of the instrument is rotated at a full 360 degrees by the free dominant hand. An arc outlined on the cervix by the sharp blade 25 is traced with the cutting wire 19. The tissue obtained should be cone shaped with a cut mark at 12 o'clock. The length and angle of the wire 19 may be selected based on the need for the depth and width of endocervical and ectocervical lesions, respectively.

The rotational movement of this cone biopsy instrument reduces blood loss associated with the surgery. A complete resection of an intact cone is accomplished in one rotation over 5–8 seconds; as opposed to the 5–10 minutes required for a knife cone biopsy. Because of the reduced time spent in cutting the tissue, the blood loss will be decreased. Furthermore, the tissue damage caused by the "sawing" or "stabbing" motion of the knife cone biopsy procedure is eliminated. The rotational movement also eliminates dangerous potential injury to the vaginal wall, further reducing the morbidity associated with LEEP cone biopsy.

Other disadvantages of LEEP cone biopsy are obviated by the use of the new instrument. Instead of various sized loops implemented in the LEEP cone biopsy, a single newly developed cone biopsy instrument would replace them. A completely resected intact cone is obtained with the new cone biopsy instrument. In contrast, multiple pieces are produced by the LEEP cone. The insulated cervical guide tip helps to accurately resect the abnormal tissue, greatly reducing potential perforation and positive internal cone margin. Due to the simplicity and speed of the procedure, use of the instrument will also relieve both the operator's and patient's anxiety associated with the cone biopsy.

I claim:

1. A cone biopsy instrument comprising in combination:
   a cuff of electrical insulating material;
   a core positioned within said cuff and having an electrical conductor;
   a wire carrier of electrical insulating material and having at least one radially projecting arm;
   an electrically conducting wire connected between said wire carrier arm and said core at an oblique angle to said core; and
   an implant sleeve carried on and freely rotating with respect to said core between said wire carrier and the tip of said instrument.

2. An instrument as defined in claim 1 wherein said implant sleeve has a plurality of barbs on the outer surface thereof.

3. An instrument as defined in claim 1 with a cervical guide tip of electrical insulating material carried on said core.

4. An instrument as defined in claim 3 including a second radially projecting arm on said wire carrier with a tissue cutting blade at the outer end of said second arm.

5. An instrument as defined in claim 3 including second and third arms projecting radially from said wire carrier substantially equally spaced around said wire carrier, with a cutting blade at the end of one of said second and third arms.

6. An instrument as defined in claim 5 with said wire carrier affixed to said cuff.

7. An instrument as defined in claim 1 with said wire carrier affixed to said cuff.

8. A cone biopsy instrument comprising in combination:
   a cuff of electrical insulating material;
   a core positioned within said cuff and having an electrical conductor;
   said cuff including a wire carrier of electrical insulating material and having at least two radially projecting arms;
   an electrically conducting wire connected between one of said wire carrier arms and said core at an oblique angle to said core;
   a tissue cutting blade at the outer end of one of said arms;
   an implant sleeve carried on and freely rotating with respect to said core between said wire carrier and the tip of said instrument; and
   a cervical guide tip of electrical insulating material carried on said core.

* * * * *